United States Patent [19]
Hood

[11] Patent Number: 5,669,922
[45] Date of Patent: Sep. 23, 1997

[54] ULTRASONICALLY DRIVEN BLADE WITH A RADIAL HOOK THAT DEFINES A CIRCULAR RECESS

[76] Inventor: Larry Hood, 25652 Nottingham Ct., Laguna Hills, Calif. 92653-7504

[21] Appl. No.: 603,059

[22] Filed: Feb. 20, 1996

[51] Int. Cl.⁶ .................................................. A61B 17/32
[52] U.S. Cl. ........................................... 606/169; 606/170
[58] Field of Search ........................... 60/169, 166, 167, 60/170

[56] References Cited

U.S. PATENT DOCUMENTS

| | | |
|---|---|---|
| 3,086,288 | 4/1963 | Balamuth et al. . |
| 5,151,084 | 9/1992 | Khek .............................. 606/169 |
| 5,261,922 | 11/1993 | Hood . |
| 5,324,299 | 6/1994 | Davison et al. . |
| 5,417,654 | 5/1995 | Kelman ............................ 606/169 |
| 5,443,474 | 8/1995 | Sfakianos et al. ................. 606/167 |

FOREIGN PATENT DOCUMENTS

WO93/14708  8/1993  WIPO .................................. 606/169

*Primary Examiner*—Michael Buiz
*Assistant Examiner*—Kevin Truong
*Attorney, Agent, or Firm*—Blakely Sokoloff Taylor & Zafman

[57] ABSTRACT

An ultrasonically driven blade which has a radial hook. The radial hook defines a recess that has a circular cross-section. The radially hook shape blade has a relatively small amount of mass located at an anti-node of the blade assembly. The relatively light anti-nodal tip provides a large energy gain and efficiently transfers ultrasonic energy to surrounding tissue. Additionally, the ultrasonic energy is transferred from the hook to tissue primarily along a longitudinal axis of the blade, thereby increasing the energy efficiency of the overall assembly.

16 Claims, 3 Drawing Sheets

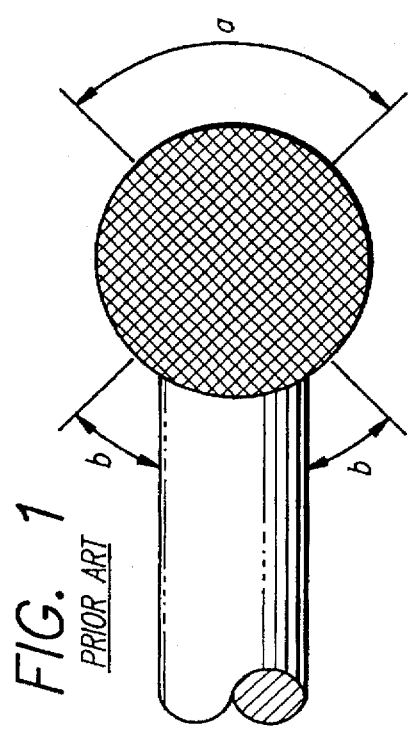
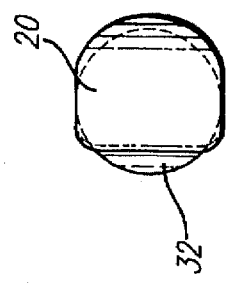
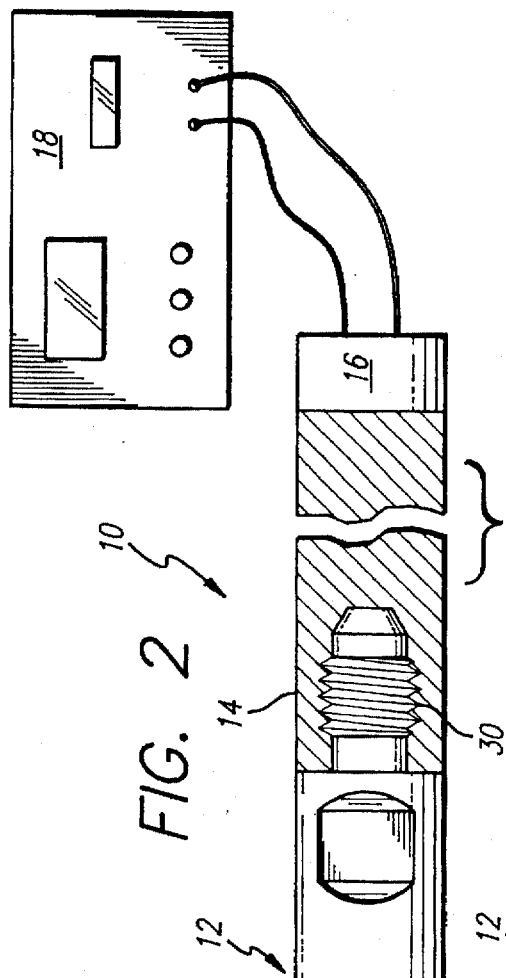
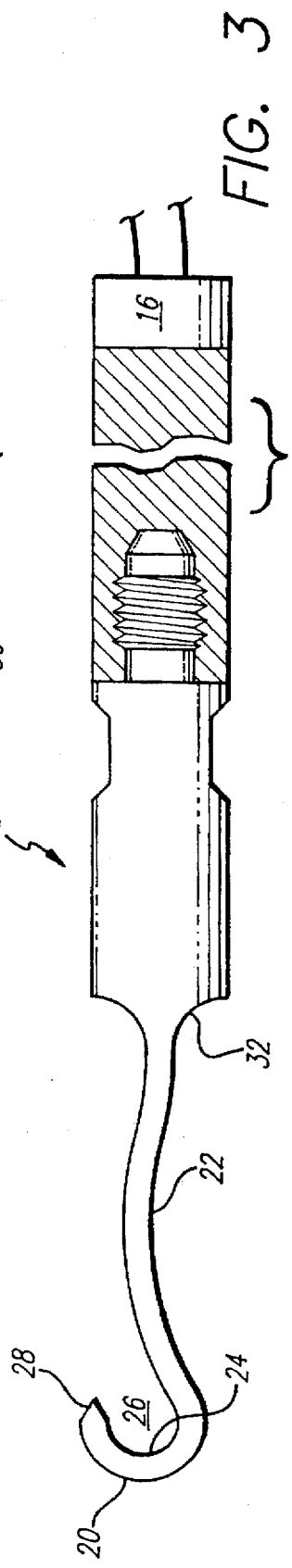

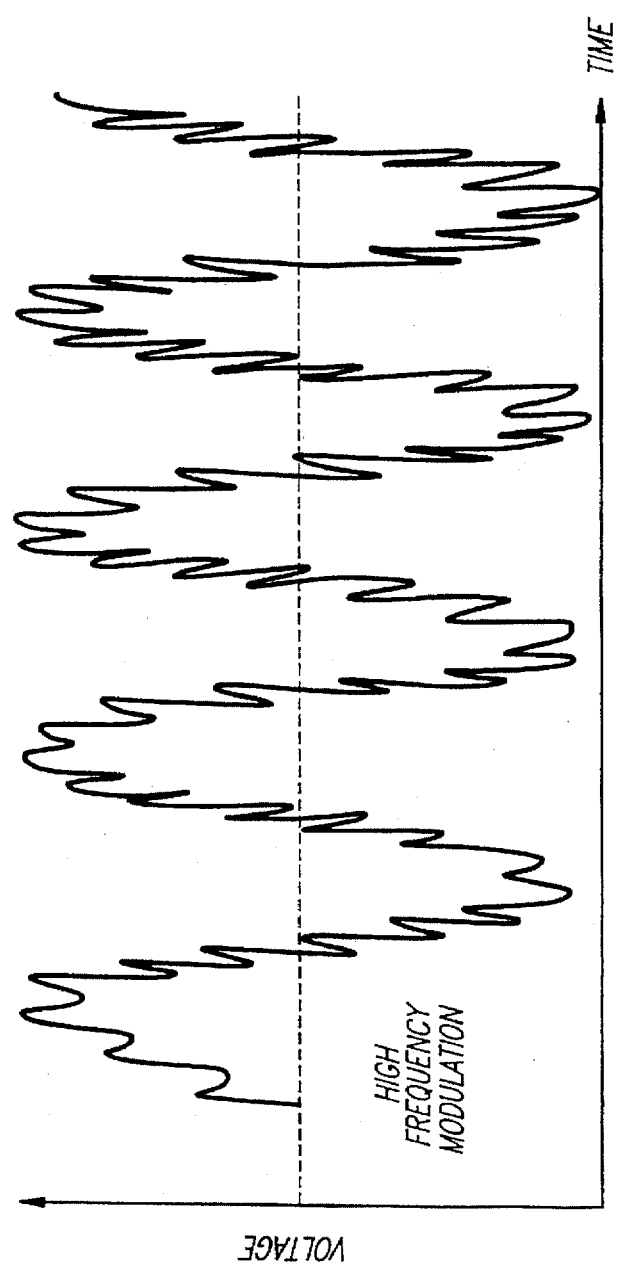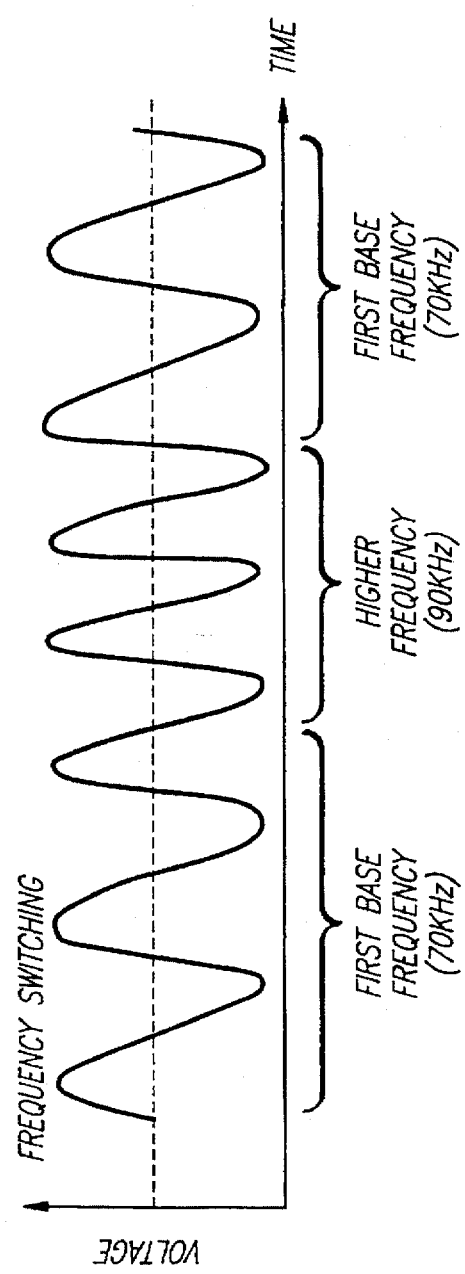

ULTRASONICALLY DRIVEN BLADE WITH A RADIAL HOOK THAT DEFINES A CIRCULAR RECESS

BACKGROUND OF THE INVENTION

1. Field of the Invention

The present invention relates to an ultrasonically driven surgical blade.

2. Description of Related Art

It has been found that the coagulation of blood can be accelerated if ultrasonic energy is applied to the blood and surrounding tissue. Ultrasonic energy can be provided by an ultrasonic blade assembly. A typical ultrasonic blade assembly includes a blade that is coupled to an ultrasonic horn. The horn moves the blade in a vibratory manner. Coagulation is accelerated by the transfer of ultrasonic energy into the tissue, and by the heat generated from the vibratory movement of the blade relative to the patient tissue.

FIG. 1 shows an existing ultrasonically driven blade with a rod and sphere type tip. The outer surface of the spherical tip is typically placed into contact with tissue to promulgate coagulation. The spherical tip has a relatively large mass which limits the energy gain of the blade. Additionally, the movement of the tip is generally directed along the longitudinal axis of the rod. The spherical shape of the tip creates a plurality of energy vectors that are not parallel with the longitudinal axis of the rod, thereby reducing the efficiency in transferring the ultrasonic energy to the tissue. It would be desirable to provide an ultrasonically driven blade that efficiently transfers ultrasonic energy to tissue.

SUMMARY OF THE INVENTION

The present invention is an ultrasonically driven blade which has a radial hook. The radial hook defines a recess that has a circular cross-section. The radially hook shape blade has a relatively small amount of mass located at an anti-node of the blade assembly. The relatively light anti-nodal tip provides a large energy gain and efficiently transfers ultrasonic energy to surrounding tissue. Additionally, the ultrasonic energy is transferred from the hook to tissue primarily along a longitudinal axis of the blade, thereby increasing the energy efficiency of the overall assembly.

BRIEF DESCRIPTION OF THE DRAWINGS

The objects and advantages of the present invention will become more readily apparent to those ordinarily skilled in the art after reviewing the following detailed description and accompanying drawings, wherein:

FIG. 1 is an ultrasonically driven surgical blade of the prior art;

FIG. 2 is a side view of a surgical blade assembly of the present invention;

FIG. 3 is a bottom view of the surgical blade;

FIG. 4 is a side view of the surgical blade;

FIG. 7a is a graph showing a waveform of a modulated acoustic wave that drives the surgical blade;

FIG. 7b is a graph showing a waveform that has a first frequency which is switched with a second frequency.

DETAILED DESCRIPTION OF THE INVENTION

Figure 5:
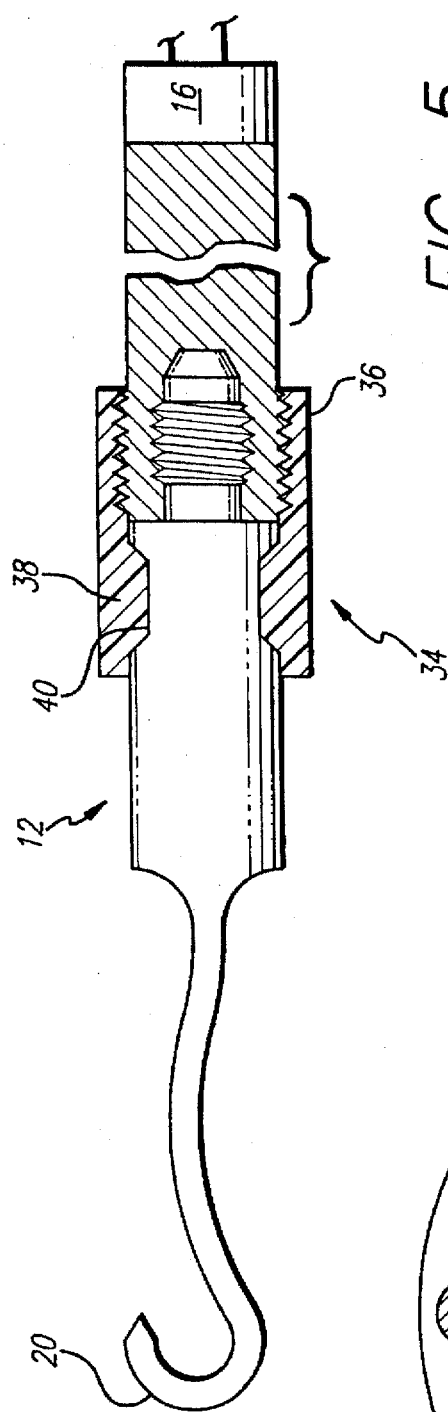
FIG. 5 is an alternate embodiment of a surgical blade with a sleeve.

Referring to the drawings more particularly by reference numbers, FIGS. 2–4 show a surgical blade assembly 10 of the present invention. The assembly is typically used to cut the tissue of a human patient. The blade assembly 10 includes a blade 12 that is coupled to an extender 14. The extender 14 is coupled to an ultrasonic horn schematically depicted as element 16. The horn 16 typically contains a transducer that converts an electrical signal into a mechanical movement of the extender 14 and the blade 12. The ultrasonic horn 16 is connected to an electronic controller 18 which provides an electrical signal that drives the blade 12.

The blade 12 has a radially shaped hook 20 that extends from an arm 22. The hook 20 defines a recess 24 which has an opening 26 and a circular cross-section. The radially shaped hook 20 is typically located at an anti-node of the assembly. The hook 20 and recess 24 provide a blade tip which has a relatively low mass and a corresponding high acoustal-mechanical gain. In one embodiment, the blade provides a 4:1 mechanical gain.

The blade 12 is typically placed into contact with tissue to induce hemostasis. The horn 16 induces a vibratory movement of the blade 12 along the longitudinal axis of the assembly. As shown in FIG. 3, to optimize the transfer of ultrasonic energy to the tissue, the assembly is typically manipulated by the user so that the side of the hook 20 is in contact with the tissue. The opening 24 and the shape of the hook 20 are such that a large proportion of the ultrasonic energy generated by the horn 16 is transferred to the tissue by the blade 12, thereby providing an efficient coagulation assembly.

The hook 20 may have a tip 28 that can be manipulated by the user to cut tissue. The blade 12 of the present invention can therefore both cut and coagulate tissue. The diameter of the hook 20 is typically no greater than the blade body. The low hook 20 profile provides a blade that can be more readily inserted into a trocar sheath (not shown) to perform non-invasive surgical procedures such as laparoscopy.

The blade 12 has an end 30 opposite from the tip 24 that is attached to the extender 14. In the preferred embodiment, the end 30 is threaded and screwed into corresponding threads of the extender 14. The base of the blade threads is preferably located at an anti-node location of the assembly 10. In the preferred embodiment, the blade 12 has a step 32 located at a node location of the assembly 10. The nodal step provides a blade which has a relatively high gain and sufficient structural integrity for operation of the blade at high excitation frequencies.

The controller 18 typically has a feedback system that senses the vibratory movement of the blade and adjust the drive signal provided to the horn 16, accordingly. The unsymmetrical shape of the hook may create a vibratory feedback signal that is out of phase with the drive signal. In the preferred embodiment, the arm 22 has a radius of curvature that offsets the unsymmetric hook and provides a feedback signal which is more in phase with the drive signal.

As shown in FIG. 5, the assembly may have a sleeve 34 that prevents the blade body 12 or extender from making contact with a trocar sleeve or non-target tissue. The sleeve 34 may be constructed from an insulative housing 36 which has a pair of spring fingers 38 which snap into corresponding grooves or wrench flats 40 of the blade body 12.

Figure 6:
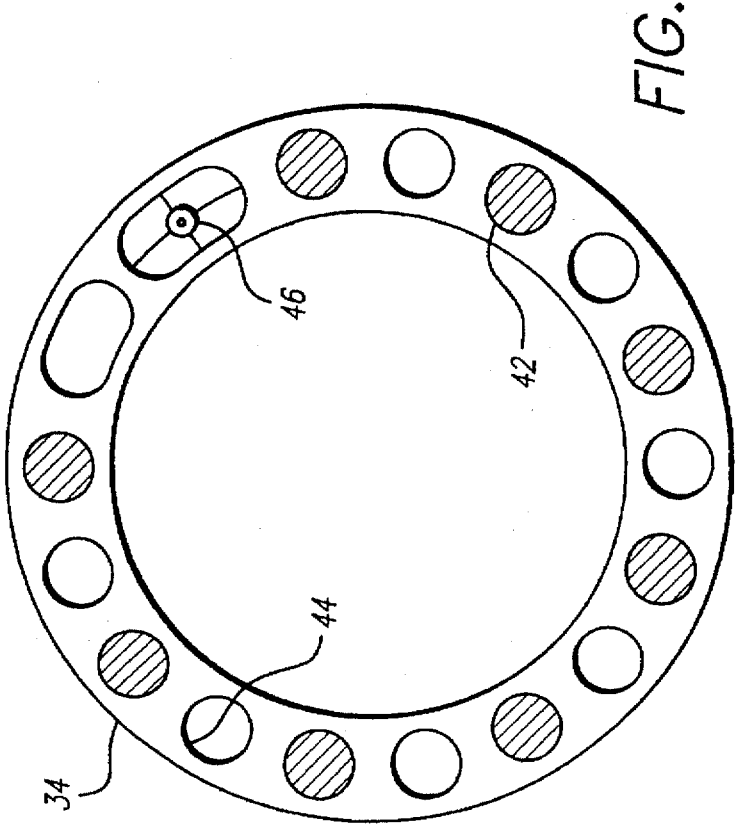
FIG. 6 is a cross-sectional view of the sleeve.

As shown in FIG. 6, the sleeve 34 may have a plurality of pins 42 and a plurality of lumens 44. The pins 42 may be connected to a voltage source of the controller 18 that applies a radio frequency voltage across alternate pins 42, and/or between the pins 42 and the blade 12. The voltage will create an electro-cautery effect that assists the coagulation of tissue. The lumens 44 may be coupled to a source of pressurized gas or liquid to blow blood, debris, etc., out of the path of the blade. Some of the lumens 40 may be coupled to an aspirator. One or more of the lumens 44 may contain a needle 46 and be coupled to a argon gas supply to create an argon beam coagulator. The combination of the low profile blade and the electro-cautery, pressurized gas, argon beam coagulator provides an assembly that can be inserted into a trocar and provide a variety of functions such as cutting, coagulating, cleaning, etc. Although the electro-cautery, pressurized gas and argon gas functions are shown together in one sleeve, it is to be understood that any one function, or combination of functions can be incorporated into the sleeve.

FIGS. 7a and 7b show waveforms of an acoustic wave that drives the blade 12. Generally speaking a higher frequency will increase the hemostatic effect and decrease the cavitation effect of the knife. Cavitation tends to atomize bodily fluids, reduce efficient cautery and decrease visibility. The upper acoustic wave frequency is limited by the anti-nodal location of the blade. A high driving frequency that does not correspond to the dimensions of the blade may cause increased stress and heat on the blade assembly. To obtain the advantages of a higher driving frequency, a relative low base wave frequency can be either modulated with a higher frequency as shown in FIG. 7a, or switched with a higher frequency as shown in FIG. 7b. In this manner, a blade assembly with dimensions that correspond to the base wave frequency can be excited with a higher frequency without generating undesirable stress and heat. Additionally, the nodal radial step of the blade provides enough structural integrity to withstand the additional stress generated by the higher frequency. The frequency typically ranges from 60,000–120,000 hertz (Hz). In the preferred embodiment, the first base frequency is 70 KHz and the second frequency is 90 KHz.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. An ultrasonic blade, comprising:
   a blade which has a proximal end, a distal end and a pair of steps located between said proximal and distal ends, said blade having a hook at said distal end and a tip the extends toward said proximal end, said blade having a uniform width from said proximal end to said distal end, and said hook having a diameter that is no greater than said blade width.

2. The blade as recited in claim 1, wherein said blade has a first anti-node located at said proximal end and a second anti-node located at said hook.

3. The blade as recited in claim 1, wherein said hook extends from an arm which has a radius of curvature.

4. The blade as recited in claim 1, further comprising a sleeve that couples said blade to an extender.

5. The blade as recited in claim 4, wherein said sleeve has a plurality of pins that are coupled to a voltage source.

6. The blade as recited in claim 4, wherein said sleeve has a plurality of lumens that are coupled to a source of pressurized air.

7. The blade as recited in claim 4, wherein said sleeve has a plurality of lumens that are coupled to a source of argon gas.

8. An ultrasonic blade assembly, comprising:
   a blade with a radial hook that defines a recess which has a circular cross-section, said hook extends from an arm that has a pair of steps located at a node of said blade; and,
   a vibrating device that vibrates said blade.

9. The assembly as recited in claim 8, wherein said vibrating device moves said blade at a first frequency that is modulated by a second frequency.

10. The assembly as recited in claim 8, wherein said vibrating device switches between a first frequency and a second frequency.

11. The assembly as recited in claim 8, wherein said blade has a first anti-node located at a coupling end and a second anti-node located at said hook.

12. The assembly as recited in claim 8, wherein said hook extends from an arm which has a radius of curvature.

13. The assembly as recited in claim 8, further comprising a sleeve that couples said blade to an extender.

14. The assembly as recited in claim 13, wherein said sleeve has a plurality of pins that are coupled to a voltage source.

15. The assembly as recited in claim 13, wherein said sleeve has a plurality of lumens that are coupled to a source of pressurized air.

16. The assembly as recited in claim 13, wherein said sleeve has a plurality of lumens that are coupled to a source of argon gas.

* * * * *